US010463519B2

(12) United States Patent
Aggerholm et al.

(10) Patent No.: US 10,463,519 B2
(45) Date of Patent: Nov. 5, 2019

(54) DELIVERY SYSTEM FOR IMPLANTABLE MEDICAL DEVICE (71) Applicant: COOK MEDICAL TECHNOLOGIES LLC, Bloomington, IN (US)

(72) Inventors: Steen Aggerholm, St. Heddinge (DK); Thomas Lysgaard, Solroed Strand (DK)

(73) Assignee: Cook Medical Technologies LLC, Bloomington, IN (US)

( * ) Notice: Subject to any disclaimer, the term of this patent is extended or adjusted under 35 U.S.C. 154(b) by 324 days.

(21) Appl. No.: 14/681,271

(22) Filed: Apr. 8, 2015

(65) Prior Publication Data
US 2015/0290007 A1    Oct. 15, 2015

(30) Foreign Application Priority Data

Apr. 9, 2014 (GB) .................................. 1406404.2

(51) Int. Cl.
A61F 2/958    (2013.01)
A61F 2/962    (2013.01)

(52) U.S. Cl.
CPC .............. A61F 2/958 (2013.01); A61F 2/962 (2013.01); A61F 2002/9583 (2013.01);
(Continued)

(58) Field of Classification Search
CPC .. A61F 2/958; A61F 2/962; A61F 2002/9583; A61F 2002/9586; A61F 2/95; A61F 2250/0048; A61M 25/1002
See application file for complete search history.

(56) References Cited

U.S. PATENT DOCUMENTS 5,409,495 A * 4/1995 Osborn ................... A61F 2/958
604/103.06
5,484,411 A * 1/1996 Inderbitzen ....... A61M 25/1002
604/103.08
(Continued)

FOREIGN PATENT DOCUMENTS

EP    0 714 640 A1    6/1996
EP    0714640 A1 *   6/1996
(Continued)

OTHER PUBLICATIONS

Great Britain Combined Examination and Search Report from corresponding Great Britain application No. GB1406404.2 dated Nov. 4, 2014 (5 pgs).

Primary Examiner — Ryan J. Severson
Assistant Examiner — Christian D Knauss
(74) Attorney, Agent, or Firm — Brinks Gilson & Lione (57) ABSTRACT A delivery system includes an inflatable delivery balloon formed with a plurality of constraining elements which create constrained regions in a body portion of the balloon, interposed between unconstrained regions. The constrained regions create recesses for receiving a medical device or part of a medical device. The constraining elements are preferably formed by woven or braided material, advantageously embedded within the wall of the inflatable balloon. The constraining elements provide a structure that will not flatten upon inflation of the balloon and also a structure which can readily be folded or wrapped for endoluminal delivery purposes, and which retains flexibility of the delivery device.

22 Claims, 5 Drawing Sheets (52) U.S. Cl.
CPC ............ *A61F 2002/9586* (2013.01); *A61F 2210/0057* (2013.01); *A61F 2230/0069* (2013.01); *A61F 2250/0048* (2013.01)

(56) References Cited

U.S. PATENT DOCUMENTS

| | | | |
|---|---|---|---|
| 5,620,457 A * | 4/1997 | Pinchasik | A61M 25/1002 |
| | | | 604/101.01 |
| 5,836,965 A | 11/1998 | Jendersee et al. | |
| 5,935,135 A * | 8/1999 | Bramfitt | A61F 2/958 |
| | | | 606/191 |
| 5,976,181 A | 11/1999 | Whelan et al. | |
| 6,010,480 A | 1/2000 | Abele et al. | |
| 6,022,359 A * | 2/2000 | Frantzen | A61F 2/958 |
| | | | 604/101.01 |
| 6,027,510 A | 2/2000 | Alt | |
| 6,048,350 A | 4/2000 | Vrba | |
| 6,110,192 A | 8/2000 | Ravenscroft et al. | |
| 6,129,706 A | 10/2000 | Janacek | |
| 6,306,162 B1 | 10/2001 | Patel | |
| 6,478,807 B1 | 11/2002 | Foreman et al. | |
| 6,764,504 B2 | 7/2004 | Wang et al. | |
| 6,942,681 B2 | 9/2005 | Johnson | |
| 7,004,963 B2 | 2/2006 | Wang et al. | |
| 7,056,323 B2 | 6/2006 | Mareiro et al. | |
| 7,083,639 B2 | 8/2006 | Guinan et al. | |
| 7,776,078 B2 | 8/2010 | Burgmeier et al. | |
| 7,879,053 B2 | 2/2011 | Trinidad | |
| 7,963,987 B2 | 6/2011 | Melsheimer et al. | |
| 8,048,028 B2 | 11/2011 | Horn et al. | |
| 8,333,000 B2 | 12/2012 | Huang et al. | |
| 2002/0120321 A1 * | 8/2002 | Gunderson | A61F 2/958 |
| | | | 623/1.11 |
| 2003/0028211 A1 * | 2/2003 | Crocker | A61F 2/86 |
| | | | 606/192 |
| 2003/0032999 A1 | 2/2003 | Huang | |
| 2004/0138731 A1 | 7/2004 | Johnson | |
| 2005/0049608 A1 | 3/2005 | Aznoian et al. | |
| 2006/0135980 A1 * | 6/2006 | Trinidad | A61M 25/1002 |
| | | | 606/191 |
| 2008/0183132 A1 * | 7/2008 | Davies | A61M 25/104 |
| | | | 604/103.09 |
| 2009/0069878 A1 * | 3/2009 | Weber | A61F 2/856 |
| | | | 623/1.11 |
| 2011/0152997 A1 | 6/2011 | Kelly et al. | |
| 2012/0059401 A1 * | 3/2012 | Konstantino | A61F 2/958 |
| | | | 606/159 |
| 2013/0116655 A1 * | 5/2013 | Bacino | A61B 17/320725 |
| | | | 604/509 |

FOREIGN PATENT DOCUMENTS

| | | |
|---|---|---|
| EP | 0 834 293 A1 | 4/1998 |
| EP | 1 132 059 A1 | 9/2001 |
| WO | WO 1997/021400 | 6/1997 |
| WO | WO 2011/112863 | 9/2011 |

\* cited by examiner

DELIVERY SYSTEM FOR IMPLANTABLE MEDICAL DEVICE

RELATED APPLICATIONS

This application claims the benefit of priority under 35 U.S.C. § 119(a) to Great Britain Patent Application No. 1406404.2, filed Apr. 9, 2014, which is incorporated by reference here in its entirety.

TECHNICAL FIELD

The present invention relates to a delivery system for delivering an implantable medical device endoluminally into a patient's vessel and in the preferred embodiment for delivering a stent or stent graft.

BACKGROUND ART

Implantable medical devices are well known in the field of endoluminal treatment of medical conditions and comprise a wide variety of types. In general, medical devices are either self-expandable or expandable by a delivery mechanism of an introducer assembly. Self-expandable devices may be made of a material having inherent expansion properties, such as spring steel or other resilient material, including metals, metal alloys and also polymers and the like. Self-expandable devices may also be made of shape memory material, such nickel titanium alloy (for instance Nitinol). Such devices will expand into a vessel as soon they are released from the delivery constraining mechanisms.

A problem with self-expandable devices is that in order to ensure their proper operation they are generally sized to apply constant pressure on the vessel walls, which over time can impair the integrity of the vessel.

Devices which are not self-expandable, that is which are expanded by a separate device, can be fitted to a vessel more precisely and more reliably, while generally avoiding some of the issues encountered with self-expanding devices. A common deployment method for such devices involves the use of an inflatable delivery balloon. The device is loaded and crimped onto the deflated and often wrapped balloon, passed endovascularly to the treatment point and then the balloon inflated to expand the device until it presses against the vessel wall. Once expanded, the balloon is deflated and removed from the patient, leaving the device implanted in the vessel. In many instances it is preferable to use such a balloon expandable medical device.

However, there are some known issues with deployment by inflatable balloons, typically sliding of the medical device during the deployment procedure, which can lead to incorrect placement of the device in the vessel, to incomplete expansion of the device and at worst to an abortive procedure. Attempts have been made to try to secure such devices to the balloon, for instance by shaping the balloon to have one or more inflatable ribs which can engage with a part of the device to hold it in position. However, ribs and other shaping features of this nature tend to flatten on inflation of the balloon, leading to loss of the holding feature. Other attempts have involved adding to the balloon one or more ridges or other protruding elements of solid form to engage the medical device. Such elements provide better retention of the medical device on the delivery balloon but usually at the expense of adding bulk to the balloon, which impairs its compressibility, as well as in some cases reducing its flexibility when deflated. A less flexible and a less compressed balloon can adversely affect the trackability of the balloon through a patient's vasculature and also the size of vessel which can be treated.

Examples of prior art balloon-based delivery devices can be found in U.S. Pat. No. 5,935,135, EP-0,714,640, US-2011/0152997, US-2002/0120321, EP-1,132,059, U.S. Pat. No. 6,942,681, US-2003/0032999, U.S. Pat. Nos. 5,836, 965, 5,976,181, 6,022,359, 6,027,510, 6,110,192, 6,764,504, US-2005/0049608 and US-2004/0138731, among others.

SUMMARY OF THE INVENTION

The present invention seeks to provide an improved delivery system for delivering an implantable medical device endoluminally into a patient's vessel and to an improved method of deploying an implantable medical device.

According to an aspect of the present invention, there is provided an endoluminal delivery device including: a catheter unit; a delivery balloon mounted on the catheter unit, the balloon including a body portion and first and second end portions coupled to the catheter unit, the body portion providing a medical device support surface; the delivery balloon being inflatable so as to cause the body portion to expand to an inflated diameter; and at least one circumferential constraining element disposed around at least a part of the body portion, the at least one circumferential constraining element acting to constrain inflation of at least one circumferential section of the body portion to a diameter less than the inflated diameter.

The provision of a constraining element could be said to provide a contoured or shaped delivery balloon by a mechanism opposite to that conventional in the art, namely by constraining a part of the balloon from expansion rather than by enlarging a part of the balloon. In practice, the balloon will expand under inflation pressure and will adopt a non-smooth shape as a result of the constraining elements, which non-smooth shape will provide device holding surfaces or shoulders. The shape will be retained irrespective of the degree of inflation of the balloon, that is the shape will not flatten as inflation pressure is increased, contrary to many types of conventional balloon. The constraining elements could have a relatively low volume structure which will not adversely affect the size of the delivery balloon and can also be made of flexible material so as not to impair the flexibility of the balloon particularly when in the deflated condition.

Advantageously, the or each constraining element is in the form of an annular band disposed circumferentially around the body portion. The constraining band or bands will help generate annular inflated ribs or ridges around the balloon, at the locations free of the constraining elements, useful for holding the implantable medical device in place.

In the preferred embodiment, the or each constraining element is in the form of an annular band of woven or braided material. A woven or braided material can readily be attached to or incorporated into the balloon wall material and can also act as a strengthening element to the balloon.

An embodiment includes a plurality of constraining elements, disposed along the body portion of the delivery balloon. Preferably, the constraining elements are spaced from one another in a longitudinal direction of the balloon, that is along its axis. The number and spacing of the constraining elements will be dependent upon the nature and size of the device to be held on and deployed by the balloon.

Advantageously, the or each constraining element is in attached to or embedded within the body portion of the balloon.

In a preferred embodiment, the device includes a sleeve coupled to the body portion of the delivery balloon, the sleeve including the constraining element or elements. The sleeve may include at least one portion having a first diameter, the or each constraining element being in the form of an annular section of the sleeve having a smaller diameter than the first diameter. The sleeve may be in the form of an integral tubular element incorporating the at least one portion and the or each constraining element. Advantageously, the sleeve includes a plurality of constraining elements separated from one another by a said portion of first diameter. In a preferred embodiment, wherein the sleeve is made of a woven or braided material, the at least one portion being woven or braided to a larger diameter than the diameter of the or each constraining element.

In another embodiment, the sleeve is differentially expandable to provide zones expanded to the first diameter and constraining zones expanded to a second diameter smaller than the first diameter.

The portion or portions of first diameter and the or each constraining element may be made from a common material but could also be made from different materials.

The sleeve could also perform as a balloon strengthening element, allowing the balloon to be inflated to higher pressures than prior art structures.

In some embodiments the balloon body portion is made from a non-conformable material while in other embodiments the balloon body portion may be made from a conformable or elastic material.

Preferably, the balloon body portion is substantially cylindrical, although in other embodiments it may have a non-cylindrical shape, for instance tapering or the like.

The catheter unit may include a single catheter provided with at least one lumen therein, the catheter including an inflation and/or deflation port disposed between the first and second end portions of the balloon. Other embodiments may have a double catheter unit.

According to another aspect of the present invention, there is provided an assembly including: an endoluminal delivery device including: a catheter unit; a delivery balloon mounted on the catheter unit, the balloon including a body portion and first and second end portions coupled to the catheter unit, the body portion providing a medical device support surface; the delivery balloon being inflatable so as to cause the body portion to expand to an inflated diameter (e.g., a first diameter); and at least one circumferential constraining element disposed around at least a part of the body portion, the at least one circumferential constraining element acting to constrain inflation of at least one circumferential section of the body portion to a diameter less than the inflated diameter (e.g., a second diameter); and a medical device disposed on the delivery balloon, wherein at least a part of the medical device is located over and held by the at least one constraining element.

The medical device may be or include a stent structure having at least one stent ring. The device may be in the form of a series of separate stent rings or elements or in the form of a series of loosely connected stent rings or elements. The structure disclosed herein could be used or designed for a variety of different designs of medical device.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Described below are various embodiments of introducer assembly for delivering a medical device into a vessel or other organ of a patient through an endoluminal procedure from a remote percutaneous entry point. The person skilled in the art will appreciate that the drawings are schematic and intended to depict only the important features and characteristics of the apparatus and method taught herein. Some elements depicted in the drawings are not to scale or in proportion with one another in order to achieve this. The skilled person will know what dimensions and proportions are typical for such elements and devices.

Figure 1:
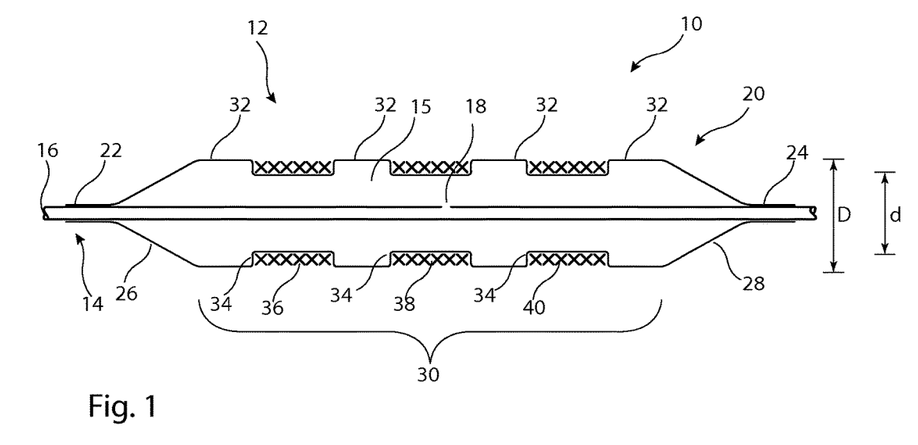
FIG. 1 is a schematic diagram in cross-section of an embodiment of delivery system holding a medical device formed of a plurality of separate stent sections.

Referring first to FIG. 1, this shows in cross-section an embodiment of delivery apparatus 10, upon which is mounted an implantable medical device 12. The delivery apparatus 10 includes a catheter unit 14, which in this embodiment is formed of a single catheter having at least one lumen 16 therein which is fluidically coupled to an outlet port 18. The catheter unit 14 may also include, usefully, at least one second lumen therethrough for the passage of a guide wire (not shown) to enable the delivery device 10 to be deployed over the wire.

A delivery balloon 20 is fitted to the catheter unit 14 and typically includes first and second end portions 22, 24 coupled to the catheter unit 14, specifically in fluid tight manner. In this example, the delivery balloon 20 includes conical sections 26, 28 located between the end portions 22, 24 and a body portion 30 of the balloon 20. The body portion 30, in the depicted embodiment, is substantially cylindrical save for radially constricted zones described in further detail below, and is substantially cylindrical in axial cross-section. The balloon includes a balloon chamber 15 in fluid communication with the port 18 of the catheter unit 14 so as to inflatable and deflatable by fluid fed through the catheter unit 14.

The body portion 30 includes non-constricted zones 32 which are able to expand radially outwardly on inflation of the delivery balloon 20 to a first inflated diameter D. The body member 30 also includes constrained sections 34, which are constrained by constraining elements described in further detail below. As will be apparent from FIG. 1, the constrained zones 34 are able to extend radially to a second diameter d less that the first inflated diameter D of the unconstrained sections 32. As a result, the constrained sections 34 create annular recesses in the delivery balloon 20, for supporting the medical device 12.

In the embodiment shown in FIG. 1, there are provided a plurality of constrained zones 34, although in other embodiments there may be a single constrained section. In this embodiment, the constrained sections 34 are spaced from one another with non-constrained zones interposed between adjacent constrained sections 34. The constrained sections 34 are, in this example, equally spaced from one another, although it is envisaged that in other embodiments the spacing of the constrained sections 34 may be different, for example may vary along the length of the delivery balloon 20, in dependence upon the nature of the medical device 12 carried on the delivery balloon 20, on the desired spacing of elements of the delivery device in the patient and so on. Similarly, the constrained sections 34 may have similar dimensions but in other embodiments may have different dimensions, for example lengths and/or expanded diameters.

In the example shown in FIG. 1, the medical device 12 includes a plurality of individual stent rings 36, 38 and 40 which are separate from one another. Each stent ring 36-40 may be made from a conventional stent structure, for example to have an undulating, zigzag or other shapes and each may be formed by a single such stent element or by a plurality of such annular stent elements coupled to on another. In other embodiments the stent rings could be a braided structure.

Medical devices 12 of such a nature, that is formed of a plurality of separate elements, can be particularly useful in the treatment of delicate vessels which require opening or recanalization and where a conventional unitary stent structure would impose undesired straightening forces on the vessel. A medical device formed of separate units will not impart any significant straightening force on the vessel and will therefore be better able to conform to any curvature in the vessel. The skilled person will appreciate, though, that a medical device formed of a plurality of separate stent elements exhibits challenges in the deployment of the medical device, for instance requiring complex delivery assemblies or multiple delivery stages. The delivery device 10 shown in FIG. 1, however, provides a plurality of annular recesses within the body portion 30 of the delivery balloon 20, each able to hold one of the stent rings 35-40, so that these can be reliably deployed in the vessel of the patient and at the desired spacing from one another. The medical device 10 can also be deployed in a single medical procedure.

Figure 2:
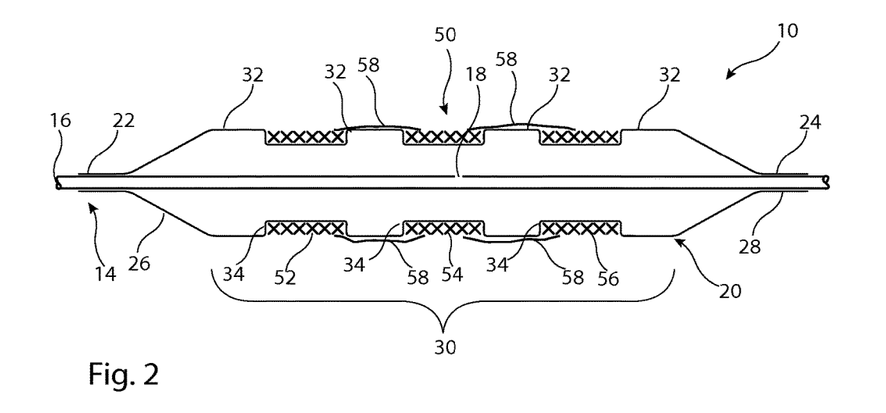
FIG. 2 is a view similar to that of FIG. 1, holding a medical device formed of a plurality of interconnected stent sections.

FIG. 2 shows another example of use of the device 10 of FIG. 1, in this case for the delivery of a medical device 50 formed of a plurality of stent rings 52-56 which in this example are connected to one another by connecting elements 58. As the stent rings 52-56 are firmly held within the constrained zones 34 of the delivery balloon 20, the connecting elements 58 need only be loose connectors, for instance threads or weak tie bars. The connecting elements 58 can usefully lie over the non-constrained zones 32 of the body portion 30 of the delivery balloon 20, although in other embodiments the unconstrained zones 32 may be provided with channels or recesses for accommodating the connecting elements 58. A medical device having weak connecting elements can be particularly advantageous for deployment in weak vessels for the reasons given above.

The delivery device 10 shown herein can be used to deliver any of a variety of medical devices including stents, stent grafts and other implantable medical devices. The size, number and disposition of the constrained zones 34 will vary in dependence upon the nature of the medical device to be carried and delivered by the delivery assembly 10. Specific designs could be readily devised by the person skilled in the art from the teachings herein.

Figure 3:
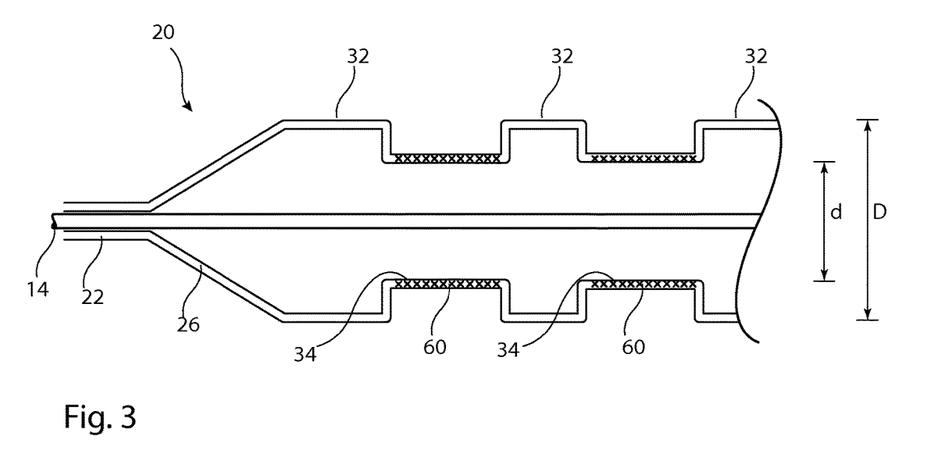
FIG. 3 is a schematic diagram in cross-section of an embodiment of delivery balloon.

Referring now to FIG. 3, this shows in schematic form and in longitudinal cross-section one embodiment of delivery balloon 20. It will be appreciated that FIG. 3 depicts only a part of the balloon 20.

The balloon 20 is formed from one or more layers of flexible material, which may be of any of the materials commonly used for medical balloons. The balloon may be made of conformable or non-conformable material, that is material which does or does not stretch when inflated to operating pressures. Embedded within the wall of the balloon 20 are a plurality of bands of, in this example, woven, knitted or braided material 60, having an annular form and a substantially consistent expanded diameter d. The bands 60 preferably do not stretch when the balloon is inflated to operating pressures, or exhibit only minimal stretch compared to the non-constrained parts of the body portion of the balloon.

The bands of constraining material 60 can usefully be embedded within the wall of the delivery balloon during the fabrication of the balloon 20. Specifically, the balloon 20 may be made from a raw tubing which is heated and inflated in a forming mold, in which the annular bands of constraining material 60 have been disposed. The mold would typically have an inner mold surface consistent with the shape of the formed balloon 20 shown in FIGS. 1 to 3. The raw tubing is heated to an extent sufficient to cause at least partial softening or reflow of the material forming the balloon, such that this material can flow around and into the bands of constraining material, thereby effectively embedding the constraining material into the balloon wall. For this purpose, the balloon wall may be formed as a single layer structure but in other embodiments may be formed from a plurality of different layers with an outer layer or layers having a lower softening or melting temperature compared to an inner layer or layers. The person skilled in the art will appreciate that it is not necessary for the entirety of the bands of constraining material to be embedded within the balloon wall and that in some cases at least part of the material of the bands may extend beyond the outer surface of the balloon wall, although this is not preferred.

Once the bands of constraining material have been embedded in the balloon wall, the structure can be deflated and eventually removed from the mold when sufficiently cooled. The structure will then be unitary.

The drawing of FIG. 3 is purely exemplary. The person skilled in the art will appreciate that it is not necessary to have right angles in the various wall sections of the balloon 20 and that in practice these are likely to be much less pronounced and typically rounded.

The structure taught herein provides a device which avoids the need for protrusions, ribs or the like, which can add bulk to the balloon and can also limit the radial compressibility of the balloon for deployment purposes. Moreover, the use of woven, knitted or braided thread in the bands 60 provides a structure which retains high levels of flexibility, enabling the balloon 20 to be wrapped and folded for delivery purposes, exhibiting behavioural characteristics in this regard which are very similar to conventional medical balloons. In this regard, the bands 60 forming the constraining elements may be made of any suitable thread, including suture thread, polyester, ultrahigh molecular weight polyester such as Dyneema and so on.

On inflation of the balloon 20, the non-constrained portions 32 will tend to bulge outwardly radially beyond the constrained zones 34, to cause recesses at the contained zones 34 useful for holding a medical device or part of a medical device.

It is preferred that at normal inflation pressures the difference in the inflated diameters of the balloon 20 between the unconstrained zones 32 and the constrained zones 34, that is the difference between D and d, is about the thickness of the medical device or part of the medical device to be held within the constrained zones 34. In practice, this difference in diameters, representative of the depth of the recess formed by the constraining elements 60, should be enough to hold the medical device or portion of medical device securely therewithin. It is not necessary, although it is preferred, for the entire thickness of the medical device or portion of medical device to be housed within the recesses.

Figure 4:
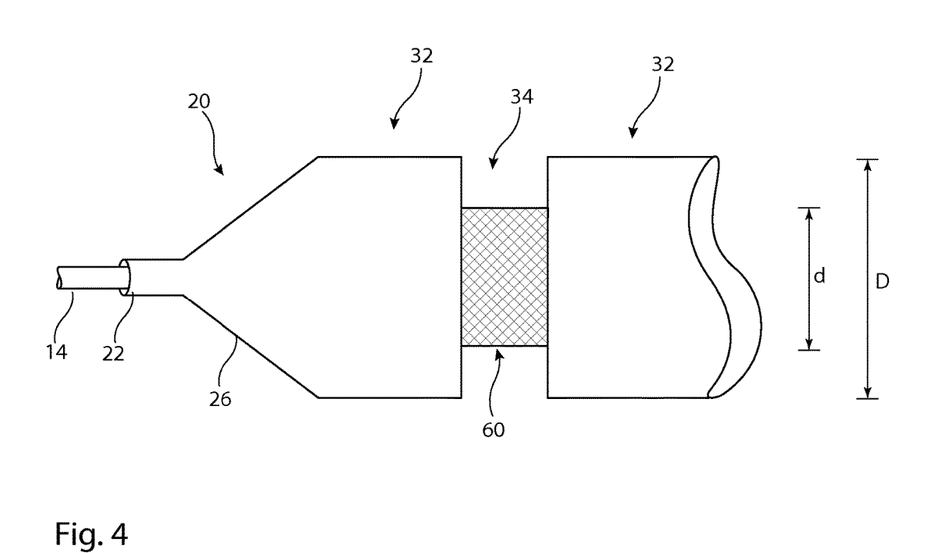
FIG. 4 is a schematic diagram of a portion of another embodiment of delivery balloon in an inflated condition.

Referring now to FIG. 4, this shows another example of medical balloon 20, in which the constraining elements 60, formed of woven, knitted or braided bands of material as in the embodiment of FIG. 3, are disposed outside of the wall of the balloon 20, rather than being embedded therewithin. It is preferred that the constraining elements 60 are fixed to the balloon wall 20, which may be by bonding, welding or even partial melting of one or both of the balloon wall and constraining element to cause these to fuse to one another.

Figure 5:
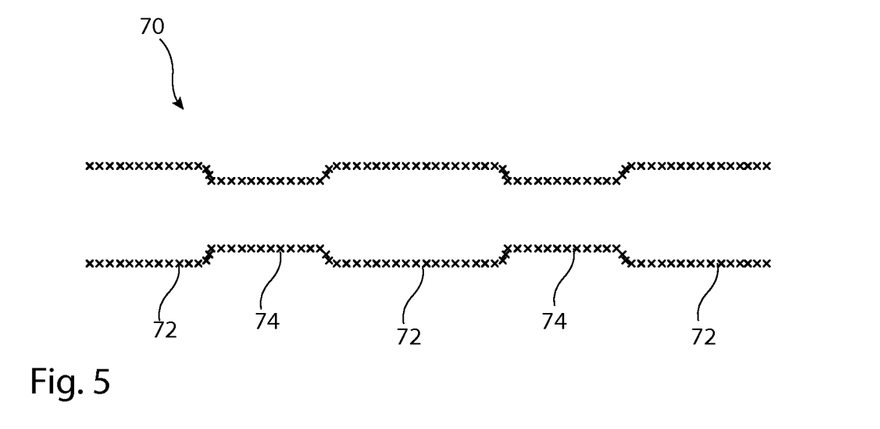
FIG. 5 is a schematic diagram in cross-section of an embodiment of sleeve for a delivery balloon.
Figure 6:
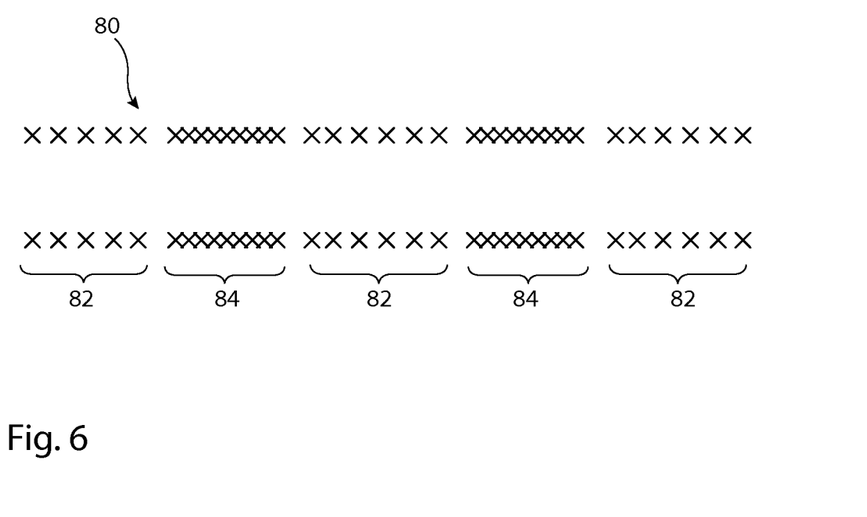
FIG. 6 is a schematic diagram in cross-section of another embodiment of sleeve for a delivery balloon.

FIGS. 5 and 6 show two different embodiments of sleeve structures which may be used in place of the constraining elements shown in FIGS. 3 and 4, that is of individual annular bands of constraining material.

FIG. 5 depicts in longitudinal cross-section a constraining sleeve 70 formed, preferably, of woven, knitted or braided threads, of which a variety of materials may be used as explained above in connection with the constraining elements 60. The sleeve 70 shown in FIG. 5 includes zones 72 which are woven or braided to a great diameter (i.e. zones of first sleeve diameter) than interleaved zones 74. The zones 72 of greater diameter would typically be disposed at the unconstrained zones 32 of a balloon 20, whereas the zones 74 of smaller diameter will be disposed at the constrained zones 34 of the balloon. The difference in diameters between the zones 72 and 74 of the sleeve 70 will create the recesses and raised areas of the body portion 30 of the delivery balloon 20. It will be appreciated that in this embodiment the entirety of the body portion 30 of the delivery balloon 20, or at least the operative part thereof, will incorporate the strengthening sleeve 70 and that the zones 32 may, on inflation of the balloon, in effect be constrained by the sleeve material at the zones 72 but nevertheless be able to expand to a greater diameter than at the zones 74. Provision of a sleeve 70 has the advantage of simple manufacture of the balloon 20 and also provides strengthening of the balloon 20, allowing the balloon 20 be inflated to greater pressures with lower or little risk of balloon burst. In this regard, in some embodiments, the sleeve 70 could also extend through the conical portions 26, 28 of the balloon and also to the necks 22, 24, providing strengthening along the entire the length of the balloon 20.

Advantageously, the material used for the sleeve 70 is non-elastic, although it is not excluded that the material could be of elastic form.

FIG. 6 shows another embodiment of sleeve 80, which is formed of first zones 82 interleaved with second zones 84. The sleeve 80 has, in this embodiment, a generally uniform diameter along its length, in contrast with the sleeve 70, which has a varying diameter between the zones 72 and 74. The sleeve 80 has a structure whereby the zones 84 will expand less during inflation of a balloon incorporating the sleeve 80. This can be achieved in several different ways. In one example, the zones 82 may have a looser weave than the zones 84. In another example, where the sleeve 80 is made of a braided structure, the braid angle in the zones 82 may be shallower than the braid angle in the zones 84, that is the zones 82 will be braided at an angle able to expand radially outwardly to a greater extent than the zones 84. In yet another example, the sleeve 80 may be made of different materials, with the zones 84 made of a material having lower elasticity than the material used to form the zones 82. This can be achieved by varying the material used during the weaving or knitting process or by forming separate annular bands and coupling these to one another, for example by suturing or the like.

When embedded in the wall of a balloon 20 (or disposed on the balloon 20), the sleeve 80 will cause the balloon 20 to expand differentially and in particular to expand less at the zones 84, thereby creating annular recesses in the surface of the balloon for accommodating a medical device or part thereof.

Figure 7:
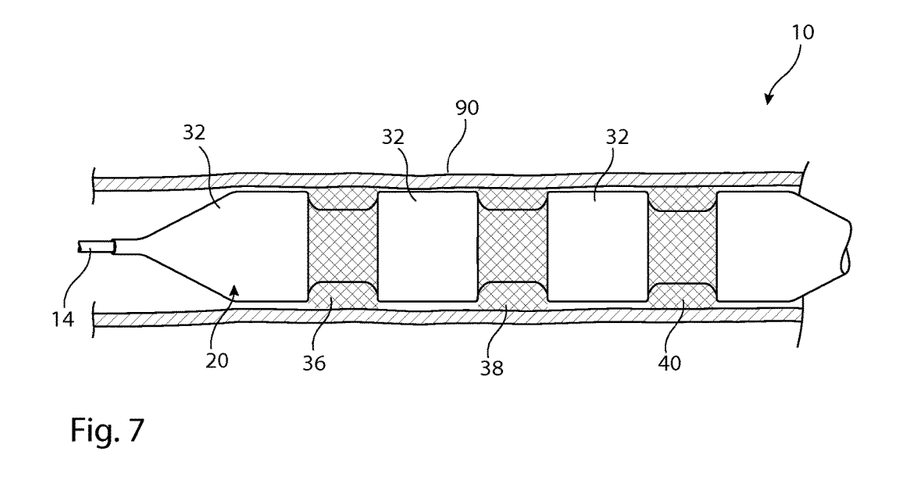
FIGS. 7 and 8 show a device deployment process using the embodiment of delivery system of FIG. 1.
Figure 8:
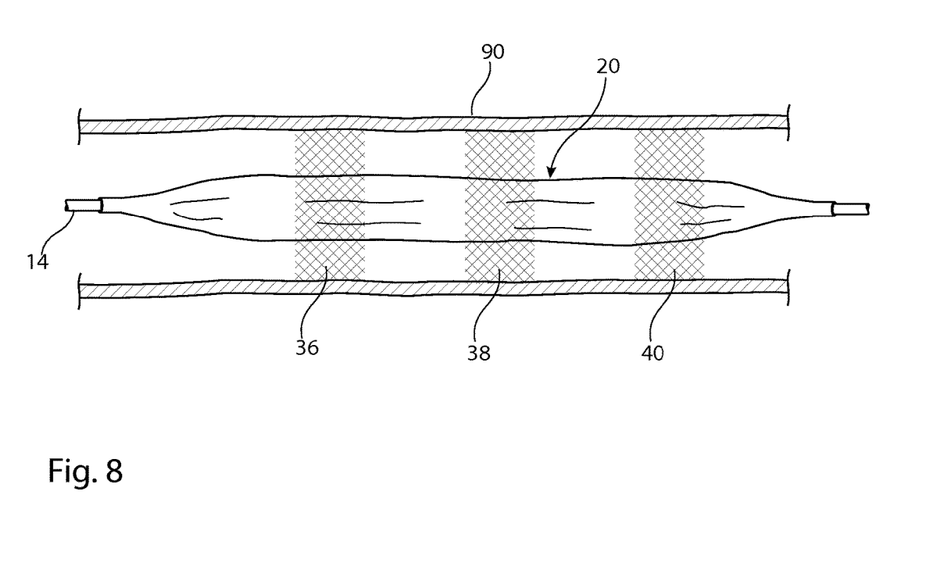

Referring now to FIGS. 7 and 8, these show the embodiment of medical balloon 20 of FIG. 1 in the process of deployment of the medical device 12 into a patient. With reference first to FIG. 7, this shows the deployment device 10 in position in vessel 90 at the target site to be treated. The deployment balloon 20 is shown in an inflated condition, achieved by feeding inflation fluid through the lumen 16 of the catheter 14, which exits through the outlet 18 shown in FIGS. 1 and 2. Any suitable inflation fluid can be used, including for instance saline solution, contrast media and so on.

On inflation of the balloon 20, the medical device 12, in this example the stent rings 36-40 which previously have been crimped onto the folded and wrapped balloon 20, are radially expanded to come into contact with the wall of the vessel 90. The portions 32 of the balloon 20 will expand radially outwardly to a greater extent than the constrained portions 34, thereby holding the stent elements 36-40 in position. In contrast with other designs of shaped balloon, where the shape of the balloon will tend to be lost due to flattening as a result of inflation pressure, the constraining elements 60 will maintain the recesses for holding the stent elements 36-40.

As shown in FIG. 8, once the stent elements 36-40 have been expanded, the balloon 20 can be deflated, whereupon the entirety of the balloon will collapse radially inwardly without leaving any protrusions or ribs which could snag against the deployed medical device, allowing the balloon 20 to be withdrawn, with the catheter 14, from the patient's vessel. As can be seen, the stent elements will be deployed in the correct locations, at the correct spacing and with minimal risk of slippage of the medical device during the deployment process.

Figure 9:
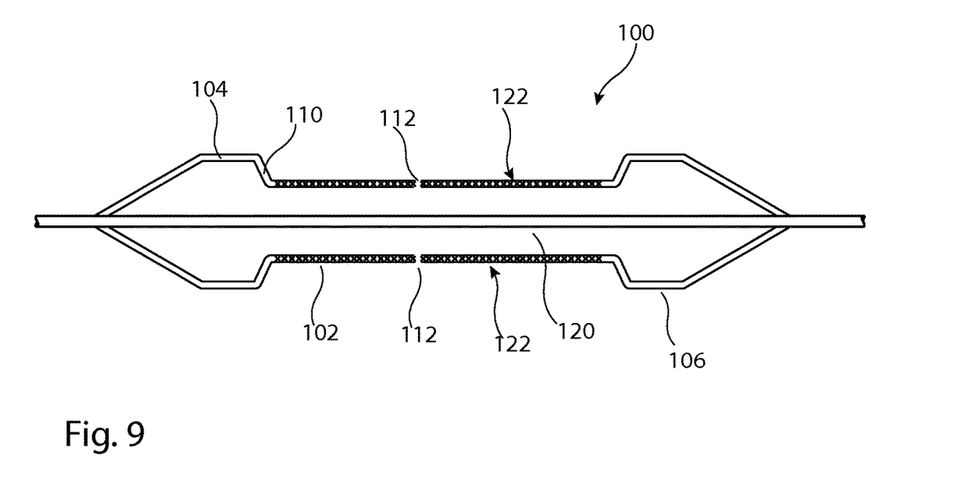
FIG. 9 is a schematic diagram in cross-section of another embodiment of a delivery balloon for administering a medicament to a patient.

Referring now to FIG. 9, this shows another embodiment of balloon assembly 100 having a constraining sleeve 102 extending along the body portion, leaving first and second unconstrained end zones 104, 106 in the body portion. The balloon wall 110 includes at least one hole or port 112 therein providing passage from the balloon chamber 120. The hole or holes 112 are sized to allow the balloon 100 to be inflated and allow for seepage of inflation fluid from the chamber into the space 122 provided by the constraining sleeve 102 between the balloon 100 and the vessel wall. When the balloon is filled with a bioactive agent, a medicament for example, the agent will be administered into the vessel between the in the space 122 and confined by the unconstrained zones 104, 106, thereby to provide targeted drug delivery into the patient. The bioactive agent can be any of the known agents. The structure shown in FIG. 9 has the advantage of providing a reliable contained vessel zone with a structure of delivery device which can be contracted, by folding and wrapping onto the delivery catheter, into a narrow diameter. It is to be understood that a balloon of this type could be produced with a plurality of drug delivery zones 122, by having a plurality of constraining sleeves 102 along the body portion, similar to the arrangement shown in FIG. 1 for instance.

The constraining sleeve or sleeves disclosed herein may usefully be made of materials having a fibre density of Dtex 55. In embodiments having fibres of different densities, these could vary around Dtex 55.

The person skilled in the art will appreciate that the structure taught herein can be useful to hold also portions of a more complex medical device, for example portions of a stent graft and so on.

It is envisaged that the constraining elements 60 could be made or include radiopaque material.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. An endoluminal delivery device including:
a catheter unit;
a delivery balloon mounted on the catheter unit, the balloon including a body portion and first and second end portions coupled to the catheter unit, the body portion providing a circumferential surface; the delivery balloon being inflatable so as to cause the body portion to expand; and
a sleeve formed on or disposed over the circumferential surface of the body portion of the delivery balloon and extending along an entire length thereof, such that the sleeve covers the entire circumferential surface of the body portion of delivery balloon, the sleeve having a structure that includes unconstrained zones and at least one constraining zone, the sleeve acting to radially constrain inflation of the body portion to an inflated, first diameter in the unconstrained zones and to a second diameter in the at least one constraining zone, wherein the second diameter is less than the inflated, first diameter, thereby causing the body portion of the delivery balloon to expand differentially to form at least one annular recess in the circumferential surface of the delivery balloon in the at least one circumferential zone, the at least one annular recess configured to hold at least one ring of a stent comprising one ring or a plurality of rings, wherein the at least one ring of the stent is disposed entirely radially within the at least one constraining zone.

2. The endoluminal delivery device according to claim 1, wherein the at least one constraining zone in the sleeve is in the form of an annular band disposed circumferentially around the body portion.

3. The endoluminal delivery device according to claim 2, wherein the at least one constraining zone is made of a first material chosen from the group of a woven, a knitted, and a braided material.

4. The endoluminal delivery device according to claim 1, comprising a plurality of constraining zones, disposed along the body portion of the delivery balloon.

5. The endoluminal delivery device according to claim 4, wherein the constraining zones are spaced from one another along the body portion of the balloon.

6. The endoluminal delivery device according to claim 1, wherein the sleeve includes at least one sleeve portion having a first sleeve diameter, the at least one constraining zone being in the form of an annular section of the sleeve having a second sleeve diameter, the second sleeve diameter being smaller than the first sleeve diameter.

7. The endoluminal delivery device according to claim 6, wherein the sleeve is in the form of an integral tubular element incorporating the at least one sleeve portion and the at least one constraining zone.

8. The endoluminal delivery device according to claim 7, wherein the sleeve includes a plurality of constraining zones separated from one another by a said sleeve portion of the first sleeve diameter.

9. The endoluminal delivery device according to claim 6, wherein the sleeve is made of a woven or braided material, the at least one sleeve portion being woven, knitted or braided to the first sleeve diameter.

10. The endoluminal delivery device according to claim 6, wherein the sleeve is differentially expandable to provide unconstrained zones expanded to the first sleeve diameter and constraining zones expanded to the second sleeve diameter smaller than the first sleeve diameter.

11. The endoluminal delivery device according to claim 6, wherein the sleeve portion or sleeve portions of first sleeve diameter and the at least one constraining zone are made from a common material.

12. The endoluminal delivery device according to claim 6, wherein the sleeve portion or sleeve portions of first sleeve diameter and the at least one constraining zone are made from different materials.

13. The endoluminal delivery device according to claim 1, wherein the balloon body portion is made from a second material chosen from the group of a non-conformable material, a conformable material, and an elastic material.

14. The endoluminal delivery device according to claim 1, wherein the balloon body portion is substantially cylindrical.

15. The endoluminal delivery device according to claim 1, wherein the catheter unit includes a single catheter provided with at least one lumen therein, the catheter including an inflation deflation port disposed between the first and second end portions of the balloon.

16. The endoluminal delivery device according to claim 15, wherein the single catheter includes a guide wire lumen.

17. An assembly including:
an endoluminal delivery device including:
a catheter unit;
a delivery balloon mounted on the catheter unit, the balloon including a body portion and first and second end portions coupled to the catheter unit, the body portion providing a circumferential surface; the delivery balloon being inflatable so as to cause the body portion to expand;
a sleeve formed on or disposed over the circumferential surface of the body portion, such that the sleeve covers the entire circumferential surface of the body portion of delivery balloon, the sleeve having a structure that includes unconstrained zones and at least one constraining zone, the sleeve acting to radially constrain inflation of the body portion to an inflated, first diameter in the unconstrained zones and to a second diameter in the at least one constraining zone, wherein the second diameter less than the inflated, first diameter, thereby causing the delivery balloon to expand differentially to form at least one annular recess in the surface of the delivery balloon in the at least one circumferential section; and a medical device comprising at least one stent ring, the medical device disposed on the delivery balloon at the at least one annular recess and entirely radially within the at least one constraining zone, wherein the difference between the first diameter and the second diameter is about a thickness of the at least one stent ring.

18. The assembly according to claim 17, wherein the medical device includes a stent structure having at least one stent ring.

19. The assembly according to claim 18, wherein the medical device includes a plurality of axially spaced stent rings.

20. The assembly according to claim 19, wherein the axially spaced stent rings are separate from one another.

21. The assembly according to claim 17, wherein the sleeve coupled to the body portion of the delivery balloon includes a plurality of constraining zones, wherein the sleeve extends along an entire length of the balloon.

22. An endoluminal delivery device including:

a catheter unit;

a delivery balloon mounted on the catheter unit, the balloon including a body portion and first and second end portions coupled to the catheter unit, the body portion providing a circumferential surface; the delivery balloon being inflatable so as to cause the body portion to expand to an inflated, first diameter; and a sleeve formed on or disposed over the circumferential surface of the body portion and extending along an entire length thereof, such that the sleeve covers the entire circumferential surface of the body portion of delivery balloon, the sleeve having a structure that includes unconstrained zones and a plurality of constraining zones, the sleeve acting to radially constrain inflation of the constraining zones of the body portion to a second diameter less than the inflated, first diameter, a ring of a stent comprising one ring or a plurality of rings, wherein the ring of the stent is disposed entirely radially within the constraining zone, wherein the difference between the first diameter and the second diameter is about the thickness of the ring of the stent.

* * * * *